United States Patent
Lim et al.

(10) Patent No.: US 9,287,509 B2
(45) Date of Patent: Mar. 15, 2016

(54) QUINACRIDONE DERIVATIVE, AND PHOTOACTIVE LAYER AND PHOTOELECTRIC CONVERSION DEVICE INCLUDING SAME

(75) Inventors: Seon-Jeong Lim, Yongin-si (KR); Kyu Sik Kim, Jeonju-si (KR); Kwang Hee Lee, Yongin-si (KR); Dong-Seok Leem, Hwaseong-si (KR); Kyung Bae Park, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 736 days.

(21) Appl. No.: 13/531,724

(22) Filed: Jun. 25, 2012

(65) Prior Publication Data

US 2013/0048958 A1 Feb. 28, 2013

(30) Foreign Application Priority Data

Aug. 26, 2011 (KR) ........................ 10-2011-0085898

(51) Int. Cl.
| | | |
|---|---|---|
| *H01L 51/54* | (2006.01) | |
| *C09K 11/06* | (2006.01) | |
| *C07D 471/04* | (2006.01) | |
| *H01L 51/00* | (2006.01) | |
| C07D 471/06 | (2006.01) | |
| C07D 487/06 | (2006.01) | |
| H01L 51/42 | (2006.01) | |

(52) U.S. Cl.
CPC .......... *H01L 51/0062* (2013.01); *C07D 471/06* (2013.01); *C07D 487/06* (2013.01); *H01L 51/424* (2013.01); *Y02E 10/549* (2013.01)

(58) Field of Classification Search
None
See application file for complete search history.

(56) References Cited

U.S. PATENT DOCUMENTS

| 5,201,961 A | 4/1993 | Yoshikawa et al. |
| 2006/0044561 A1* | 3/2006 | Nii ................................ 356/434 |
| 2007/0120045 A1 | 5/2007 | Yokoyama |

FOREIGN PATENT DOCUMENTS

| JP | 2000-315579 A | 11/2000 |
| JP | 2007-067194 A | 3/2007 |
| WO | WO-2005017046 A2 | 2/2005 |

OTHER PUBLICATIONS

Schulze et al. Adv. Mater. 2006, 18, 2872-2875. Year of publicaiton: 2006.*
Adhikari et al. J. Org. Chem. 2009, 74, 3341-3349. Date of web publication: Mar. 30, 2009.*

* cited by examiner

*Primary Examiner* — Andrew K Bohaty
(74) *Attorney, Agent, or Firm* — Harness, Dickey & Pierce, P.L.C.

(57) ABSTRACT

A quinacridone derivative may be represented by Chemical Formula 1, and a photoactive layer may include the same. A photoelectric conversion device may include a first electrode, a second electrode spaced apart from and configured to face the first electrode, and the photoactive layer including the quinacridone derivative between the first electrode and the second electrode.

26 Claims, 4 Drawing Sheets

QUINACRIDONE DERIVATIVE, AND PHOTOACTIVE LAYER AND PHOTOELECTRIC CONVERSION DEVICE INCLUDING SAME

PRIORITY STATEMENT

This application claims priority to and the benefit of Korean Patent Application No. 10-2011-0085898 filed in the Korean Intellectual Property Office on Aug. 26, 2011, the entire contents of which are incorporated herein by reference.

BACKGROUND

1. Field

Example embodiments recite a quinacridone derivative, and a photoactive layer and a photoelectric conversion device including the same.

2. Description of the Related Art

Generally, a photoelectric conversion device refers to a device for converting light into an electrical signal using photoelectric effects. The photoelectric conversion device may have been applied to various photosensors, e.g., an automobile sensor, a home sensor, a solar cell, and/or a photodiode. Thereby, research on improving the photoelectric conversion efficiency of a photoelectric conversion device may have been performed.

SUMMARY

Example embodiments provide a quinacridone derivative that selectively and efficiently absorbs light in a predetermined or given wavelength range, and may have improved thermal stability and light absorption performance.

Example embodiments also provide a photoactive layer including the quinacridone derivative, and a photoelectric conversion device including the photoactive layer.

According to example embodiments, a quinacridone derivative may be represented by the following Chemical Formula 1.

[Chemical Formula 1]

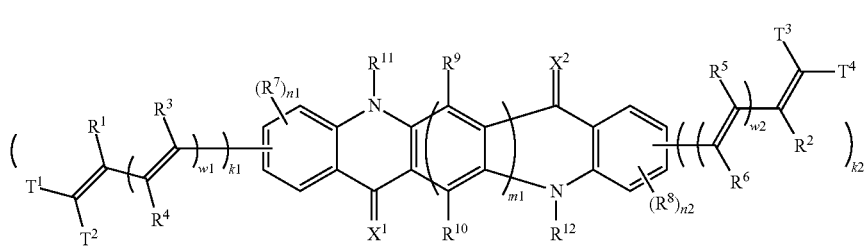

In Chemical Formula 1,
$T^1$ to $T^4$ may be one of same and different, and each of $T^1$ to $T^4$ may be independently one of a cyano group (CN), a halogen, a substituted or unsubstituted $C_6$ to $C_{30}$ aryl group, and a substituted or unsubstituted $C_2$ to $C_{30}$ heteroaryl group, for example, a cyano group (CN) and a halogen. $X^1$ and $X^2$ may be one of same and different, and each of $X^1$ and $X^2$ may be independently one of oxygen (O), sulfur (S), and $C(CN)_2$, for example, one of oxygen (O) and sulfur (S).

$R^1$ to $R^{10}$ may be one of same and different, and each of $R^1$ to $R^{10}$ are independently hydrogen, a substituted or unsubstituted $C_1$ to $C_{30}$ alkyl group, a substituted or unsubstituted $C_3$ to $C_{30}$ cycloalkyl group, a cyano group (CN), a halogen, a substituted or unsubstituted $C_6$ to $C_{30}$ aryl group, and a substituted or unsubstituted $C_2$ to $C_{30}$ heteroaryl group, for example, one of hydrogen, a substituted or unsubstituted $C_1$ to $C_{10}$ alkyl group, a substituted or unsubstituted $C_3$ to $C_{10}$ cycloalkyl group, a cyano group (CN), and a halogen.

w1 and w2 may be each independently an integer ranging from 0 to 5, for example, an integer of 0 or 1. k1 and k2 may be each independently an integer ranging from 1 to 4, for example, an integer of 1 or 2. n1 and n2 may be each independently an integer ranging from 0 to 3. m1 may be an integer ranging from 1 to 5, for example, an integer ranging from 1 to 3.

$R^{11}$ and $R^{12}$ may be one of same and different, and each of $R^{11}$ and $R^{12}$ are independently one of hydrogen, a substituted or unsubstituted $C_1$ to $C_{30}$ alkyl group, and a substituted or unsubstituted $C_1$ to $C_{30}$ cycloalkyl group, for example, one of hydrogen, a substituted or unsubstituted $C_1$ to $C_{10}$ alkyl group, and a substituted or unsubstituted $C_3$ to $C_{10}$ cycloalkyl group.

The quinacridone derivative may include one selected from compounds according to Chemical Formula 2-1 to Chemical Formulas 2-10, and a combination thereof.

[Chemical Formula 2-1]

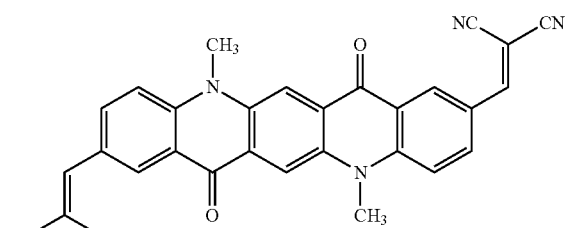

-continued

[Chemical Formula 2-2]

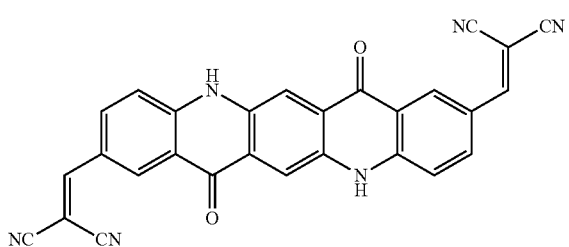

-continued

[Chemical Formula 2-3]
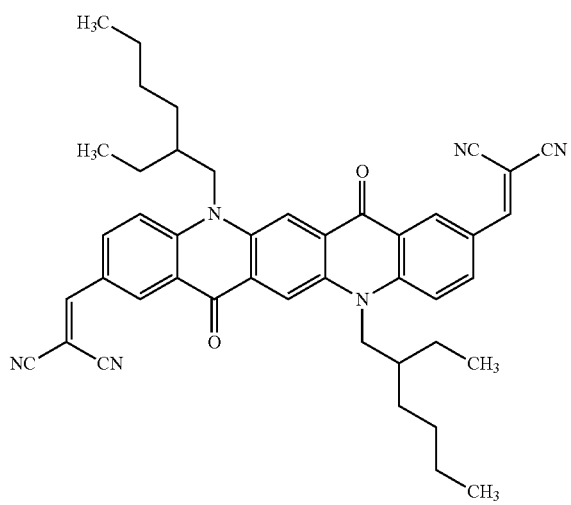

[Chemical Formula 2-4]
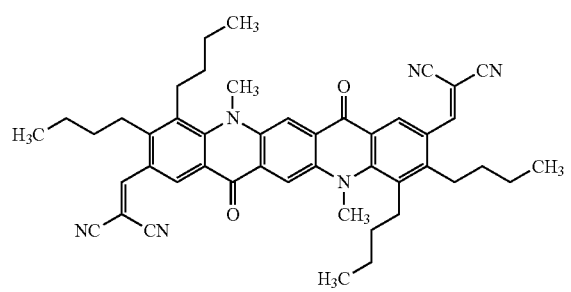

[Chemical Formula 2-5]
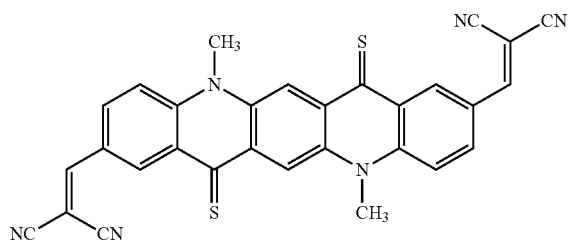

[Chemical Formula 2-6]
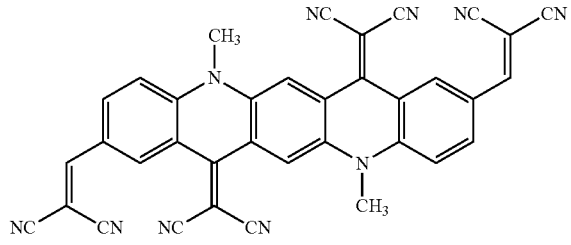

[Chemical Formula 2-7]
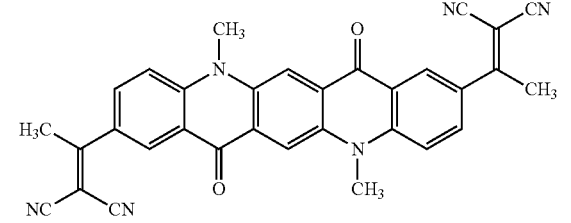

[Chemical Formula 2-8]
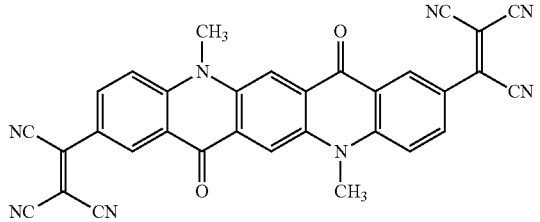

[Chemical Formula 2-9]
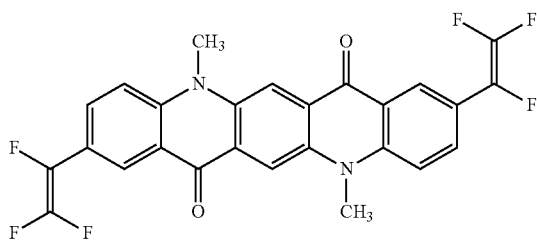

[Chemical Formula 2-10]
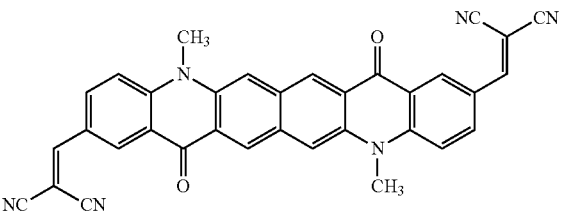

The quinacridone derivative may have a LUMO (lowest unoccupied molecular orbital) level ranging from about −2.0 eV to about −5.0 eV. The quinacridone derivative may have a bandgap ranging from about 1.5 eV to about 3.5 eV. The quinacridone derivative may absorb a light in a wavelength ranging from about 400 nm to about 700 nm. The quinacridone derivative may have a maximum absorption wavelength ranging from about 500 nm to about 600 nm. The quinacridone derivative may have a maximum molar absorption coefficient ranging from about $5.0 \times 10^2$ $cm^{-1} \cdot M^{-1}$ to about $1.0 \times 10^6$ $cm^{-1} M^{-1}$.

According to example embodiments, a photoactive layer may include the quinacridone derivative.

According to example embodiments, a photoelectric conversion device may include a first electrode, a second electrode spaced apart from and configured to face the first electrode, and a photoactive layer including the quinacridone derivative between the first electrode and the second electrode.

The photoactive layer may include one selected from a p layer, an i layer, an n layer, and a combination thereof. When the quinacridone derivative is a p-type material, an n-type material may have a LUMO level lower than about −5.0 eV. The quinacridone derivative may be included in one selected from the p layer, i layer, and a combination thereof, and the n-type material may be included in one selected from the i layer, n layer, and a combination thereof.

When the quinacridone derivative is an n-type material, a p-type material may have a LUMO level higher than −2.0 eV. The quinacridone derivative may be included in one selected from the i layer, n layer, and a combination thereof, and the p-type material may be included in one selected from the p layer, i layer, and a combination thereof.

The photoelectric conversion device may be a photodiode, a solar cell, a photovoltaic cell, an image sensing device, a photodetector, a photosensor, or an organic light emitting diode (OLED).

BRIEF DESCRIPTION OF THE DRAWINGS

Example embodiments will be more clearly understood from the following detailed description taken in conjunction with the accompanying drawings. FIG. 1 is the schematic cross-sectional view of a photoelectric conversion device according to example embodiments.

FIG. 2 shows a $^1$H NMR spectrum of the quinacridone derivative according to Example 1.

FIG. 3 shows a $^{13}$C NMR spectrum of the quinacridone derivative according to Example 1.

FIG. 4 shows ultraviolet visible ray (UV-Vis) absorption spectra of the quinacridone derivatives according to Example 1 and Comparative Example 1.

Figure 1:
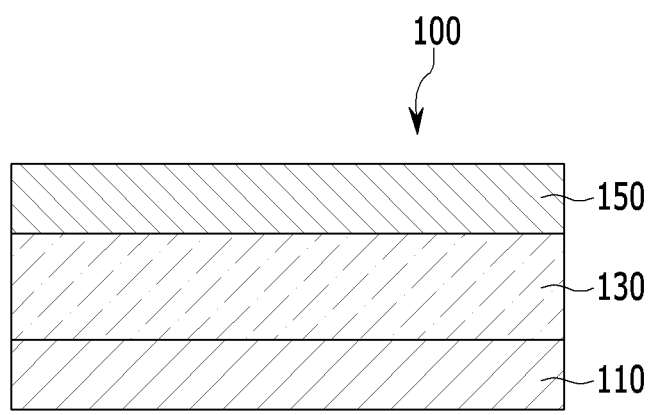
FIGS. 1-4 represent non-limiting, example embodiments as described herein

It should be noted that these Figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. For example, the relative thicknesses and positioning of molecules, layers, regions and/or structural elements may be reduced or exaggerated for clarity. The use of similar or identical reference numbers in the various drawings is intended to indicate the presence of a similar or identical element or feature.

DETAILED DESCRIPTION

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Like numbers indicate like elements throughout. As used herein the term "and/or" includes any and all combinations of one or more of the associated listed items.

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises", "comprising", "includes" and/or "including," if used herein, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

As used herein, when a specific definition is not otherwise provided, the term "substituted" refers to one substituted with at least one substituent selected from one of a halogen (—F, —Cl, —Br, or —I), a hydroxy group, a nitro group, a cyano group, an amino group ($NH_2$, $NH(R^{200})$, or $N(R^{201})(R^{202})$, wherein $R^{200}$, $R^{201}$, and $R^{202}$ may be one of same and different, and each of $R^{200}$, $R^{201}$, and $R^{202}$ may be independently one of a $C_1$ to $C_{10}$ alkyl group), an adidino group, a hydrazine group, a hydrazone group, a carboxyl group, a substituted or unsubstituted alkyl group, a substituted or unsubstituted haloalkyl group, a substituted or unsubstituted alkoxy group, a substituted or unsubstituted alkenyl group, a substituted or unsubstituted alkynyl group, a substituted or unsubstituted aryl group, a substituted or unsubstituted heteroaryl group, and a substituted or unsubstituted heterocycloalkyl group in place of at least one hydrogen of a functional group.

As used herein, when a specific definition is not otherwise provided, the term "alkyl group" may refer to a $C_1$ to $C_{30}$ alkyl group, specifically a $C_1$ to $C_{20}$ alkyl group, and more specifically a $C_1$ to $C_{10}$ alkyl group, the term "cycloalkyl group" may refer to a $C_3$ to $C_{30}$ cycloalkyl group, specifically a $C_3$ to $C_{20}$ cycloalkyl group, and more specifically a $C_3$ to $C_{10}$ cycloalkyl group, the term "alkenyl group" may refer to a $C_2$ to $C_{30}$ alkenyl group, specifically a $C_2$ to $C_{20}$ alkenyl group, and more specifically a $C_2$ to $C_{10}$ alkenyl group, the term "alkynyl group" may refer to a $C_2$ to $C_{30}$ alkynyl group, specifically a $C_2$ to $C_{20}$ alkynyl group, and more specifically a $C_2$ to $C_{10}$ alkynyl group, the term "alkoxy group" may refer to a $C_1$ to $C_{30}$ alkoxy group, specifically a $C_1$ to $C_{20}$ alkoxy group, and more specifically a $C_1$ to $C_{10}$ alkoxy group, the term "aryl group" may refer to a $C_6$ to $C_{30}$ aryl group, specifically a $C_6$ to $C_{20}$ aryl group, and more specifically a $C_6$ to $C_{15}$ aryl group, the term "heteroaryl group" may refer to a $C_2$ to $C_{30}$ heteroaryl group, specifically a $C_2$ to $C_{20}$ heteroaryl group, and more specifically a $C_2$ to $C_{15}$ heteroaryl group, the term "heterocycloalkyl group" may refer to a $C_2$ to $C_{30}$ heterocycloalkyl group, specifically a $C_2$ to $C_{20}$ heterocycloalkyl group, and more specifically a $C_2$ to $C_{15}$ heterocycloalkyl group, and the term "halogen" may refer to F, Cl, Br, or I.

As used herein, when a definition is not otherwise provided, the terms "heterocycloalkyl group" and "heteroaryl group" may independently refer to a cycloalkyl group and an aryl group including one to three heteroatoms of N, O, S, Si, or P and the remainder being carbon in one cyclic structure.

As used herein, when a definition is not otherwise provided, "combination" generally refers to mixing or copolymerization. As used herein, when a definition is not otherwise provided, the term "copolymerization" refers to block copolymerization, random copolymerization, or graft copolymerization, and the term "copolymer" refers to a block copolymer, a random copolymer, or a graft copolymer.

As used herein, when a definition is not otherwise provided in the specification, "i layer" is made of a mixture of a p-type material and an n-type material and forms a PN junction, and plays a role of receiving light, producing excitons, and separating the excitons into holes and electrons. Herein, the p-type material may be the same as or different from a material forming a p layer. The n-type material may be the same as or different from a material forming an n layer. The "p layer" may include a p-type material, and the holes separated from excitons produced may be transported thereto. The "n layer" may include an n-type material, and the electrons separated from excitons produced may be transported thereto.

In the drawings, the thickness of layers, films, panels, regions, etc., may be exaggerated for clarity. Like reference numerals designate like elements throughout the specification. It will be understood that when an element such as a layer, film, or substrate is referred to as being "on" another element, it can be directly on the other element or intervening elements may also be present.

According to example embodiments, a quinacridone derivative may be represented by the following Chemical Formula 1.

In Chemical Formula 1, $T^1$ to $T^4$ may be one of same and different, and each of $T^1$ to $T^4$ may be independently one of a cyano group (CN), a halogen, a substituted or unsubstituted $C_6$ to $C_{30}$ aryl group, and a substituted or unsubstituted $C_2$ to $C_{30}$ heteroaryl group, for example, one of a cyano group (CN) and a halogen, e.g., a cyano group (CN). $X^1$ and $X^2$ may be one of same and different, and each of $X^1$ and $X^2$ may be independently one of oxygen (O), sulfur (S), and $C(CN)_2$, for example, one of oxygen (O) and sulfur (S), e.g., oxygen (O).

$R^1$ to $R^{10}$ may be one of same and different, and each of $R^1$ to $R^{10}$ may be independently one of hydrogen, a substituted or unsubstituted $C_1$ to $C_{30}$ alkyl group, a substituted or unsubstituted $C_3$ to $C_{30}$ cycloalkyl group, a cyano group (CN), a halogen, a substituted or unsubstituted $C_6$ to $C_{30}$ aryl group, and a substituted or unsubstituted $C_2$ to $C_{30}$ heteroaryl group, for example, one of hydrogen, a substituted or unsubstituted $C_1$ to $C_{10}$ alkyl group, a substituted or unsubstituted $C_3$ to $C_{10}$ cycloalkyl group, a cyano group (CN), and a halogen, e.g., one of hydrogen, a substituted or unsubstituted $C_1$ to $C_5$ alkyl group, and a cyano group (CN).

w1 and w2 may be each independently an integer ranging from 0 to 5, for example, an integer of 0 or 1, e.g., 0. k1 and k2 may be each independently an integer ranging from 1 to 4, for example, an integer of 1 or 2, e.g., 1. n1 and n2 may be each independently an integer ranging from 0 to 3. m1 is an integer ranging from 1 to 5, for example, an integer ranging from 1 to 3, e.g., an integer of 1 or 2.

$R^{11}$ and $R^{12}$ may be one of same and different, and each of $R^{11}$ and $R^{12}$ may be independently one of hydrogen, a substituted or unsubstituted $C_1$ to $C_{30}$ alkyl group, and a substituted or unsubstituted $C_3$ to $C_{30}$ cycloalkyl group, for example, one of hydrogen, a substituted or unsubstituted $C_1$ to $C_{10}$ alkyl group, and a substituted or unsubstituted $C_3$ to $C_{10}$ cycloalkyl group, e.g., one of hydrogen and a substituted or unsubstituted $C_1$ to $C_5$ alkyl group.

The quinacridone derivative represented by the above Chemical Formula 1 may include an electron accepting functional group at both ends of a main chain and an electron donating functional group at the center of the main chain. Because the quinacridone derivative may include both the electron accepting functional group and the electron donating functional group in a molecule, the quinacridone derivative may increase a photo-transition dipole moment, and thus, have a higher light absorption coefficient.

In addition, because the quinacridone derivative represented by the above Chemical Formula 1 may include an electron accepting functional group at both ends of a main chain, the electron accepting functional group may decrease LUMO (lowest unoccupied molecular orbital) and HOMO (highest occupied molecular orbital) levels of the quinacridone derivative, in other words, the electron accepting functional group may increase the electron volt (eV) absolute value, and decrease the bandgap of the quinacridone deriva-

[Chemical Formula 1]

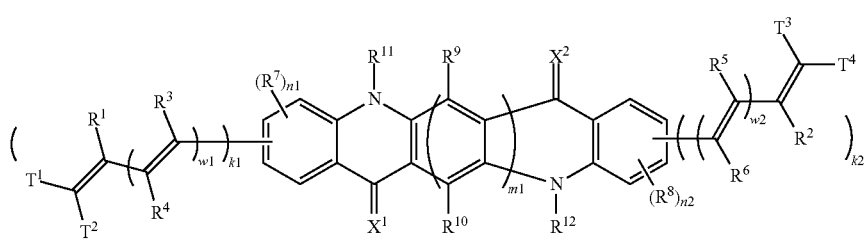

tive. Accordingly, the quinacridone derivative may effectively absorb light in a visible ray region, for example, in a region of about 400 nm to about 700 nm, e.g., in a region of about 500 nm to about 600 nm, and may have higher external quantum efficiency (EQE), thereby effectively improving photoelectric conversion efficiency.

Particularly, the quinacridone derivative according to the above Chemical Formula 1 may include one selected from compounds according to Chemical Formula 2-1 to Chemical Formulas 2-10, and a combination thereof, but is not limited thereto.

[Chemical Formula 2-1]

[Chemical Formula 2-2]

[Chemical Formula 2-3]

[Chemical Formula 2-4]

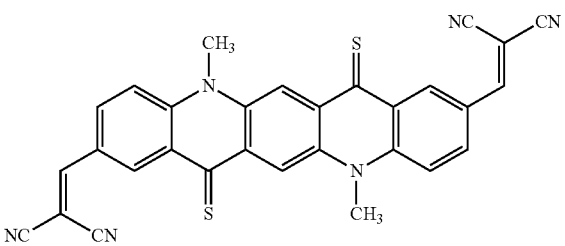
[Chemical Formula 2-5]

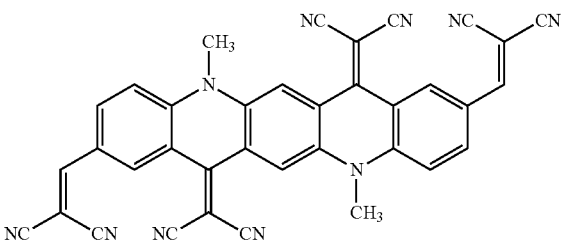
[Chemical Formula 2-6]

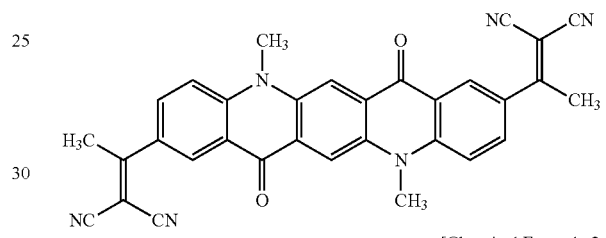
[Chemical Formula 2-7]

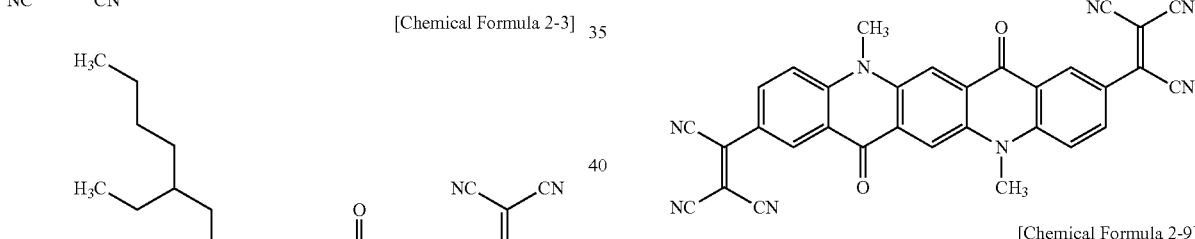
[Chemical Formula 2-8]

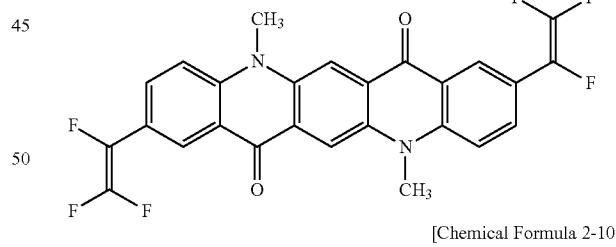
[Chemical Formula 2-9]

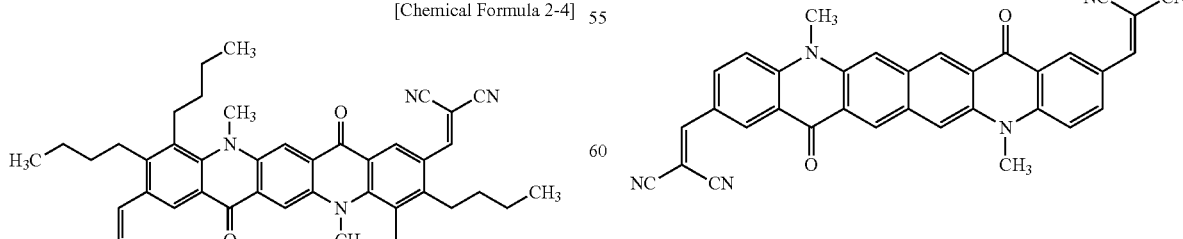
[Chemical Formula 2-10]

The quinacridone derivative may have a LUMO level ranging from about −2.0 eV to about −5.0 eV. When the quinacridone derivative has a LUMO level within the range, the quinacridone derivative may have higher external quantum efficiency (EQE), and thus, effectively improve photoelectric conversion efficiency, and may be included in one selected from a p layer, an i layer, an n layer, and a combination thereof. For example, the quinacridone derivative may have a LUMO level ranging from about −3.0 eV to about −4.6 eV, e.g., from about −3.4 eV to about −4.6 eV.

The quinacridone derivative may have a bandgap ranging from about 1.5 eV to about 3.5 eV. When the quinacridone derivative has a bandgap within the range, the quinacridone derivative may effectively absorb light in a visible ray region, for example, in a region ranging from about 400 nm to about 700 nm, e.g., in a region of about 500 nm to about 600 nm, and may have a selective photoelectric conversion characteristic for green light in the visible ray region. For example, the quinacridone derivative may have a bandgap ranging from about 1.7 eV to about 3.1 eV, e.g., from about 2.0 eV to about 2.5 eV.

The quinacridone derivative may absorb light in a wavelength region ranging from about 400 nm to about 700 nm and may have a maximum absorption wavelength ranging from about 500 nm to about 600 nm. Accordingly, the quinacridone derivative may effectively absorb light with a particular wavelength range in a visible ray region, and thus may have a photoelectric conversion characteristic for light in a particular wavelength range due to absorption wavelength selectivity and photoelectric conversion selectivity, thereby effectively improving photoelectric conversion efficiency.

The quinacridone derivative may have a maximum molar absorption coefficient ranging from about $5.0 \times 10^2$ cm$^{-1}$·M$^{-1}$ to about $1.0 \times 10^6$ cm$^{-1}$·M$^{-1}$. Accordingly, the quinacridone derivative may effectively absorb light in a particular wavelength range and improve photoelectric conversion efficiency. In particular, the quinacridone derivative may have a maximum molar absorption coefficient ranging from about $1.0 \times 10^4$ cm$^{-1}$·M$^{-1}$ to about $1.0 \times 10^6$ cm$^{-1}$·M$^{-1}$, for example, about $4.0 \times 10^4$ cm$^{-1}$·M$^{-1}$ to about $1.0 \times 10^5$ cm$^{-1}$·M$^{-1}$.

According to example embodiments, a photoactive layer may include the quinacridone derivative.

According to example embodiments, a photoelectric conversion device may include a first electrode, a second electrode spaced apart from and configured to face the first electrode, and a photoactive layer that includes the quinacridone derivative between the first and second electrodes.

Hereinafter, a photoactive layer and a photoelectric conversion device according to example embodiments are illustrated referring to FIG. 1.

FIG. 1 is, a schematic cross-sectional view of a photoelectric conversion device according to example embodiments. Hereinafter, for better understanding and ease of description, the light-receiving surface of a photoactive layer 130 that receives light may be referred to as a front side, and the opposite side may be referred to as a rear side.

Referring to FIG. 1, a photoelectric conversion device 100 according to example embodiments may include a front electrode 150 and a rear electrode 110 spaced apart by a predetermined or given interval and facing each other, and a photoactive layer 130 disposed between the rear electrode 110 and the front electrode 150.

The rear electrode 110 may include a metal or a transparent conductive material. The metal may include one selected from Al, Cu, Ti, Au, Pt, Ag, Cr, Li, and a combination thereof, the transparent conductive material may include one selected from ITO (indium tin oxide), indium-doped ZnO (IZO), aluminum-doped ZnO (AZO), gallium-doped ZnO (GZO), antimony-doped tin oxide (ATO), fluorine-doped tin oxide (FTO), tin oxide (SnO$_2$), ZnO, and a combination thereof, but are not limited thereto.

When the rear electrode 110 may include a metal, the rear electrode 110 may be formed as a semitransparent electrode with a thickness equal to or less than about 20 nm, but is not limited thereto.

The front electrode 150 may include a transparent conductive material. Unless mentioned otherwise, the transparent conductive material may be the same as described above.

The front electrode 150 may have an equal or higher work function than the rear electrode 110, but is not limited thereto. When the front electrode 150 has a higher work function than the rear electrode 110, electrons separated from excitons obtained from the photoactive layer 130 may be collected into the rear electrode 110, and holes separated from the excitons may be collected into the front electrode 150.

The photoactive layer 130 may convert light into electrical signals using the photoelectric effect, and may include the quinacridone derivative represented by the above Chemical Formula 1.

The photoactive layer 130 may include one selected from a p layer, an i layer, an n layer, and a combination thereof. The photoactive layer 130 may convert light into an electrical signal using photoelectric effects.

The p layer may contact the front electrode 150, the n layer may contact the rear electrode 110, and the i layer may contact one selected from the p layer, the n layer, and a combination thereof. However, example embodiments are not limited thereto. The p layer and the n layer may not be formed, and the i layer may contact the front electrode 150 and the rear electrode 110.

Herein, the quinacridone derivative may be included in one selected from the p layer, the i layer, the n layer, and a combination thereof.

For example, when the quinacridone derivative is a p-type material, an n-type material may have a lower LUMO level than the quinacridone derivative, for example, a larger electron volt (eV) absolute value. Herein, the quinacridone derivative may be included in one selected from the p layer, the i layer, and a combination thereof, and the n-type material may be included in one selected from the i layer, the n layer, and a combination thereof, which may form a photoactive layer 130.

As another example, when the quinacridone derivative is an n-type material, a p-type material may have a higher LUMO level than the quinacridone derivative, for example, a smaller electron volt (eV) absolute value. Herein, the quinacridone derivative may be included in one selected from the i layer, the n layer, and a combination thereof, and the p-type material may be included in one selected from the p layer, the i layer, and a combination thereof, which may form a photoactive layer 130.

The i layer may include one selected from a bulk heterojunction (BHJ), an organic/inorganic hybrid layer, and a combination thereof, but is not limited thereto.

The bulk heterojunction may include at least two selected from the quinacridone derivative according to the above Chemical Formula 1, polyaniline, polypyrrole, polythiophene, poly(p-phenylene-vinylene), poly(2-methoxy-5-(2'-ethyl-hexyloxy)-1,4-phenylene-vinylene) (MEH-PPV), poly(2-methoxy-5-(3,7-dimethyloctyloxy)-1,4-phenylene-vinylene) (MDMO-PPV), pentacene, poly(3,4-ethylene-dioxythiophene) (PEDOT), poly(3-alkylthiophene), phthalocyanine, triarylamine, benzidine, pyrazoline, styrylamine, hydrazone, carbazole, thiophene, pyrrole, phenanthrene, tetracene, naphthalene, fullerene (C60, C70, C74, C76, C78, C82, C84, C720, and C860), 1-(3-methoxy-carbonyl)propyl-1-phenyl(6,6)C61 (PCBM), C71-PCBM, C84-PCBM, bis- PCBM, perylene, derivatives thereof, and combinations thereof, but are not limited thereto.

When using materials having different energy levels from each other when providing a bulk heterojunction, a material having a relatively low LUMO level may be used for an n-type material, and a material having a relatively high LUMO level may be used for a p-type material.

The organic/inorganic hybrid layer may include an organic material selected from the quinacridone derivative represented by the above Chemical Formula 1, polyaniline, polypyrrole, polythiophene, poly(p-phenylene-vinylene), poly[2-methoxy-5-(2'-ethyl-hexyloxy)-1,4-phenylene-vinylene) (MEH-PPV), poly(2-methoxy-5-(3,7-dimethyloctyloxy)-1,4-phenylene-vinylene) (MDMO-PPV), pentacene, poly(3,4-ethylene-dioxythiophene) (PEDOT), poly(3-alkylthiophene), phthalocyanine, triarylamine, benzidine, pyrazoline, styrylamine, hydrazone, carbazole, thiophene, pyrrole, phenanthrene, tetracene, naphthalene, fullerene (C60, C70, C74, C76, C78, C82, C84, C720, and C860), 1-(3-methoxy-carbonyl)propyl-1-phenyl(6,6)C61 (PCBM), C71-PCBM, C84-PCBM, bis-PCBM, perylene, a derivative thereof, and a combination thereof, but is not limited thereto, and an inorganic semiconductor selected from CdS, CdTe, CdSe, ZnO, and combinations thereof, but is not limited thereto. When using materials having different energy levels from each other when providing an organic/inorganic hybrid layer, a material having a relatively low LUMO (lowest unoccupied molecular orbital) level may be used for an n-type material, and a material having relatively high LUMO level may be used for a p-type material.

When the i layer with the p layer and the n layer and a combination thereof forms a photoactive layer, a material for the p layer may be a p-type material used for the i layer, and a material for the n layer may be an n-type material for the i layer. However, example embodiments are not limited thereto, a p-type material for the i layer may differ from a p-type material for the p layer, and an n-type material for the i layer may differ from an n-type material for the n layer.

For example, when a material for the p layer is a p-type material for the i layer, and a material for the n layer is a n-type material for the i layer, the p and i layers may have lower interface resistance, thereby transporting holes faster and improving photoelectric conversion efficiency. In addition, the i and n layers may have lower interface resistance, thereby transporting electrons faster and improving photoelectric conversion efficiency.

The p layer and n layer may include a photoactive material that may be selected from the quinacridone derivative according to the above Chemical Formula 1, polyaniline, polypyrrole, polythiophene, poly(p-phenylene-vinylene), poly(2-methoxy-5-(2'-ethyl-hexyloxy)-1,4-phenylene-vinylene) (MEH-PPV), poly(2-methoxy-5-(3,7-dimethyloctyloxy)-1,4-phenylene-vinylene) (MDMO-PPV), pentacene, poly(3,4-ethylene-dioxythiophene) (PEDOT), poly(3-alkylthiophene), phthalocyanine, triarylamine, benzidine, pyrazoline, styrylamine, hydrazone, carbazole, thiophene, pyrrole, phenanthrene, tetracene, naphthalene, fullerene (C60, C70, C74, C76, C78, C82, C84, C720, and C860), 1-(3-methoxy-carbonyl)propyl-1-phenyl(6,6)C61 (PCBM), C71-PCBM, C84-PCBM, bis-PCBM, perylene, CdS, CdTe, CdSe, ZnO, derivatives thereof, and combinations thereof, but is not limited thereto.

When the photoactive layer may include both the p and n layers, a material with a relatively lower LUMO level among the photoactive materials may form an n layer, while a material with a relatively higher LUMO level among the photoactive materials may form a p layer.

The photoactive layer 130 may have a thickness of about 10 nm to about 200 nm. When the photoactive layer 130 has a thickness within the aforementioned range, the photoactive layer 130 may effectively absorb light to be converted into electricity, effectively separate the excitons into holes and electrons, and effectively transfer the holes and electrons separated from excitons, so as to effectively improve the photoelectric conversion efficiency. For example, the photoactive layer 130 may have a thickness of about 10 nm to about 100 nm.

Although not shown in FIG. 1, one selected from an electron transport layer (ETL), a hole blocking layer (HBL), and a combination thereof may be formed between the rear electrode 110 and the photoactive layer 130, and one selected from a hole transport layer (HTL), an electron blocking layer (EBL), and a combination thereof may be formed between the front electrode 150 and the photoactive layer 130.

The electron transport layer (ETL) may play a role of facilitating the transport of electrons, and may include one selected from 1,4,5,8-naphthalene-tetracarboxylic dianhydride (NTCDA), bathocuproine (BCP), LiF, Alq$_3$, Gaq$_3$, Inq$_3$, Znq$_2$, Zn(BTZ)$_2$, BeBq$_2$, and a combination thereof, but is not limited thereto.

The hole blocking layer (HBL) may play a role of prohibiting the transport of holes and simultaneously play a role of a protective layer for preventing or inhibiting an electrical short, and may include one selected from 1,4,5,8-naphthalene-tetracarboxylic dianhydride (NTCDA), bathocuproine (BCP), LiF, Alq$_3$, Gaq$_3$, Inq$_3$, Znq$_2$, Zn(BTZ)$_2$, BeBq$_2$, and a combination thereof, but is not limited thereto.

The hole transporting layer (HTL) may play a role of facilitating the transport of holes, and may include one selected from poly(3,4-ethylene-dioxythiophene):poly(styrene-sulfonate) (PEDOT:PSS), polyarylamine, poly(N-vinylcarbazole), polyaniline, polypyrrole, N,N,N',N'-tetrakis (4-methoxyphenyl)-benzidine (TPD), 4-bis[N-(1-naphthyl)-N-phenyl-amino]biphenyl (α-NPD), 4,4',4"-tris(N-3-methylphenyl-N-phenylamino)triphenylamine (m-MTDATA), 4,4',4"-tris(N-carbazolyl)-triphenylamine (TCTA), and a combination thereof, but is not limited thereto.

The electron blocking layer (EBL) may play a role of prohibiting the transport of electrons, and may include one selected from poly(3,4-ethylene-dioxythiophene):poly(styrene-sulfonate) (PEDOT:PSS), polyarylamine, poly(N-vinylcarbazole), polyaniline, polypyrrole, N,N,N',N'-tetrakis (4-methoxyphenyl)-benzidine (TPD), 4-bis[N-(1-naphthyl)-N-phenyl-amino]biphenyl (α-NPD), 4,4',4"-tris(N-3-methylphenyl-N-phenylamino)triphenylamine (m-MTDATA), 4,4',4"-tris(N-carbazolyl)-triphenylamine (TCTA), and a combination thereof, but is not limited thereto.

Accordingly, the photoelectric conversion device including a photoactive layer including the quinacridone derivative may be a photodiode, a solar cell (or a photovoltaic cell), an image sensing device, a photodetector, a photosensor, or an organic light emitting diode (OLED), but is not limited thereto.

EXAMPLES

The following examples illustrate this disclosure in more detail. However, example embodiments are not limited thereto.

Example 1

Preparation of Quinacridone Derivative

A quinacridone derivative is prepared according to the following Reaction Scheme 1.

[Reaction Scheme 1]

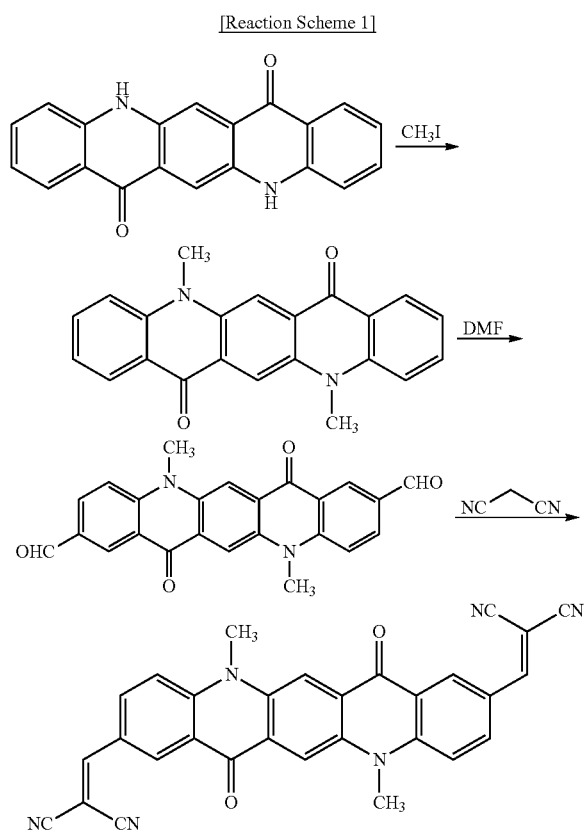

First Step: Synthesis of N,N'-dimethylquinacridone 30 ml of toluene is placed into a 100 ml round-bottomed flask, and 1 mmol of quinacridone and 4 mmol of tetrabutylammonium iodide are added thereto and dissolved therein. While the solution is fervently agitated, 1 ml of 50% NaOH and 2.4 mmol of 1-iodomethane are slowly added thereto.

The mixture is refluxed and heated for about 26 hours. 10 ml of water is used to complete the reaction, and the reactant is filtrated. Through the filtration, an organic layer is separated, and a solvent is removed under reduced pressure.

The obtained crude product is dissolved in dichloromethane, and the solution is purified through column chromatography, preparing N,N'-dimethylquinacridone. Herein, the yield is 25%.

$^1$H NMR (600 MHz, CDCl$_3$) Calcd.: δH 7.56 (d, 2H), 7.42 (m, 2H), 6.87 (m, 2H), 6.70 (d, 2H), 6.69 (s, 2H), 3.20 (s, 6H)

MS: m/z 340.12 (100.0%), 341.12 (24.5%), 342.13 (3.2%)
Chemical Formula: $C_{22}H_{16}N_2O_2$.
Anal. Calcd.: C, 77.63; H, 4.74; N, 8.23; O, 9.40.

Second Step: Synthesis of N,N'-dimethyl-2,9-diformylquinacridone 2 mmol of phosphorus oxychloride is added to 4 mmol of agitated N,N-dimethylformamide (DMF) at 0° C. in a dropwise fashion. The mixture is agitated at 0° C. for 1 hour and further agitated at room temperature for 1 hour.

1 mmol of N,N'-dimethylquinacridone dissolved in dichloroethane is added to the reactant. The mixture is agitated at 90° C. for 2 hours. The agitated reactant is cooled down and poured into cold water. The mixture is neutralized to have a pH of 7 using a 2 N NaOH aqueous solution and extracted with dichloromethane.

The extract is washed with a large amount of a saline solution, and its solvent is removed under reduced pressure. The residue is purified through silica gel column chromatography using dichloromethane/n-hexane mixed in a volume ratio of 5/1, preparing N,N'-dimethyl-2,9-diformylquinacridone. Herein, the yield is 53%.

$^1$H NMR (600 MHz, CDCl$_3$) Calcd.: δH 9.88 (s, 2H), 7.37 (s, 2H), 7.29 (d, 2H), 6.89 (d, 2H), 6.69 (s, 2H), 3.20 (s, 6H)

MS: m/z 396.11 (100.0%), 397.11 (26.7%), 398.12 (4.1%)
Chemical Formula: $C_{24}H_{15}N_2O_4$.
Anal. Calcd.: C, 72.72; H, 4.07; N, 7.07; O, 16.14.

Third Step: Synthesis of N,N'-dimethyl-2,9-bis(dicyanoethenyl)quinacridone

A mixture of 1 mmol of N,N'-dimethyl-2,9-diformylquinacridone and 2 mmol of malononitrile is added to 10 ml of ethanol, and Ni nanoparticles (diameter ranging from 15 nm to 20 nm, 10 mol %) as a catalyst are added thereto.

The mixture is agitated at room temperature for 30 minutes, diluted with 10 ml of dichloromethane, and washed with water three times and with a saline solution. An obtained organic layer is dried under anhydrous sodium sulfate (Na$_2$SO$_4$), and the solvent therein is removed under reduced pressure using a rotary evaporator.

The resulting reactant is recrystallized with ethyl acetate, preparing N,N'-dimethyl-2,9-bis(dicyanoethenyl)quinacridone represented by the following Chemical Formula 2-1, which is a red crystalline powder. Herein, the yield is 93%.

$^1$H NMR (600 MHz, CDCl$_3$) Calcd.: δH 7.87 (d, 2H), 7.79 (s, 2H), 6.86 (s, 2H), 6.65 (d, 2H), 6.69 (s, 2H), 3.20 (s, 6H)

MS: m/z 492.13 (100.0%), 493.14 (32.7%), 494.14 (5.6%), 493.13 (2.2%)
Chemical Formula: $C_{30}H_{16}N_6O_2$.
Anal. Calcd.: C, 73.16; H, 3.27; N, 17.06; O, 6.50.

[Chemical Formula 2-1]

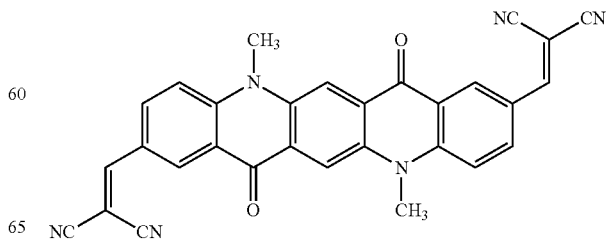

Comparative Example 1

Quinacridone Derivative

A compound according to the following Chemical Formula 3 is used as a quinacridone derivative.

[Chemical Formula 3]

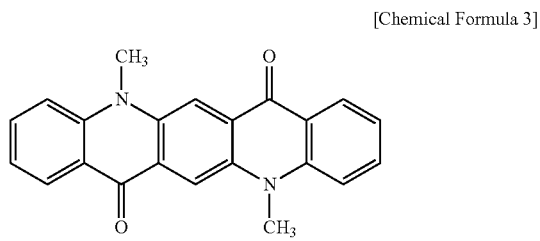 [SMILES: Cn1c2ccccc2c(=O)c2cc3c(cc21)c(=O)c1ccccc1n3C]

Experimental Example 2

NMR Measurement

The quinacridone derivative according to Example 1 is analyzed regarding $^1$H NMR and $^{13}$C NMR. The results are respectively provided in FIGS. 2 and 3.

Figure 2:
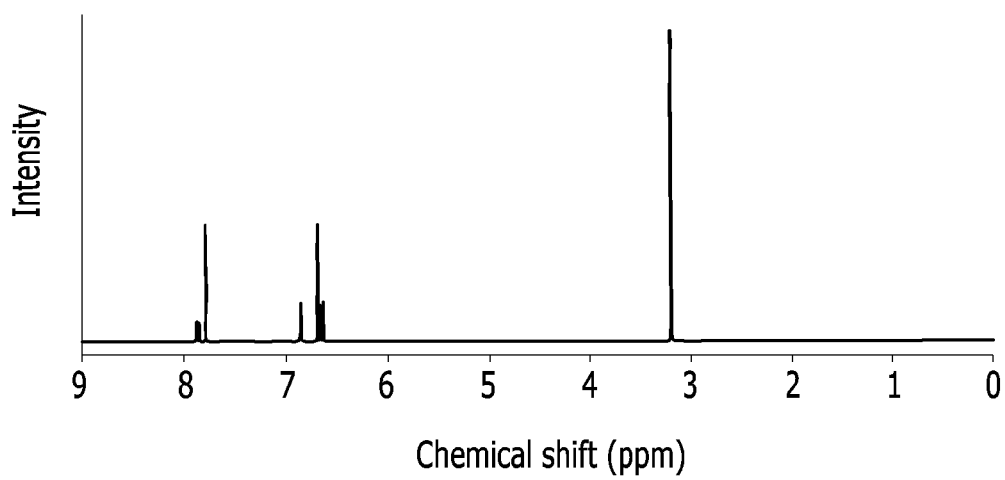

FIG. 2 shows peaks in the following Chemical Formula 4, identifying the quinacridone derivative according to Example 1 to be a resulting material according to Reaction Scheme 1.

[Chemical Formula 4]

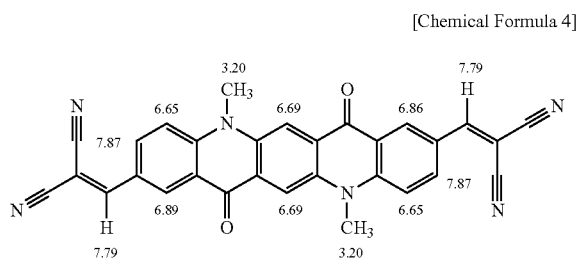 [SMILES: Cn1c2ccc(C=C(C#N)C#N)cc2c(=O)c2cc3c(cc21)c(=O)c1cc(C=C(C#N)C#N)ccc1n3C]

Figure 3:
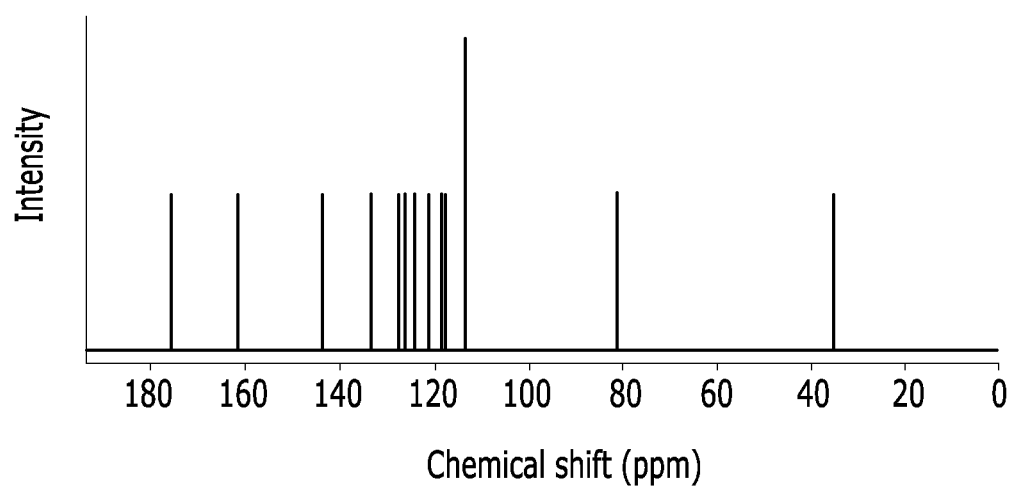

In addition, FIG. 3 shows peaks in the following Chemical Formula 5, identifying the quinacridone derivative of Example 1 to be a resulting material according to Reaction Scheme 1.

[Chemical Formula 5]

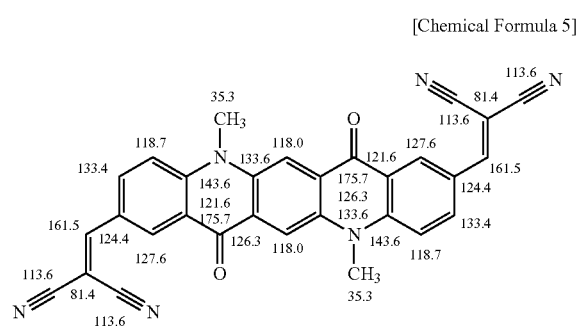 [SMILES: Cn1c2ccc(C=C(C#N)C#N)cc2c(=O)c2cc3c(cc21)c(=O)c1cc(C=C(C#N)C#N)ccc1n3C]

Experimental Example 2

Bandgap Measurement

The quinacridone derivatives according to Example 1 and Comparative Example 1 are respectively measured regarding HOMO and LUMO levels and bandgap in a cyclic voltammetry (CV) method. The results are provided in the following Table 1.

TABLE 1

|  | HOMO (eV) | LUMO (eV) | Bandgap (eV) |
| --- | --- | --- | --- |
| Example 1 | −6.16 | −3.17 | 2.99 |
| Comparative Example 1 | −5.25 | −2.13 | 3.12 |

As shown in Table 1, the quinacridone derivative of Example 1 may have a smaller bandgap than the quinacridone derivative of Comparative Example 1.

Experimental Example 3

Light Absorption Characteristic Evaluation

The quinacridone derivatives according to Example 1 and Comparative Example 1 are respectively dissolved in dichlorobenzene, and each solution is dripped on a glass plate. The solutions are dried to remove a solvent therein, obtaining films. The films are evaluated regarding each ultraviolet visible ray (UV-Vis) absorption spectrum using Cary 5000 UV spectroscopy equipment made by Varian, Inc.

Figure 4:
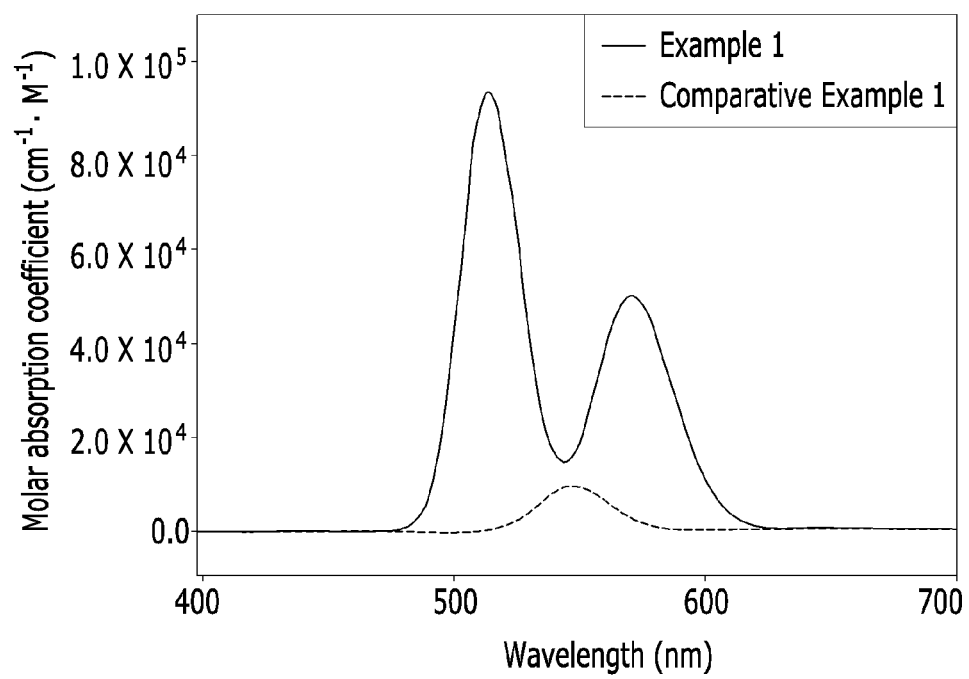

The results are provided in FIG. 4. As shown in FIG. 4, the quinacridone derivative of Example 1 may have maximum absorption wavelengths of about 520 nm and about 580 nm, and a maximum molar absorption coefficient of about $1.0 \times 10^5$ cm$^{-1}$·M$^{-1}$. In addition, the quinacridone derivative of Example 1 sufficiently absorbs light in a wavelength region ranging from about 450 nm to about 650 nm.

On the other hand, the quinacridone derivative of Comparative Example 1 may have a maximum molar absorption coefficient of about $1.0 \times 10^4$ cm$^{-1}$·M$^{-1}$, and partly absorbs light in a wavelength region ranging from about 500 nm to about 600 nm. Resultantly, the quinacridone derivative of Example 1 may have a relatively small bandgap and an improved light absorption characteristic.

While this disclosure has been described in connection with what is presently considered to be example embodiments, it is to be understood that the inventive concepts are not limited to the disclosed embodiments, but, on the contrary, is intended to cover various modifications and equivalent arrangements included within the spirit and scope of the appended claims.

What is claimed is:

1. A photoelectric conversion device, comprising:
   a first electrode;
   a second electrode spaced apart from and configured to face the first electrode; and
   a photoactive layer between the first electrode and the second electrode, the photoactive layer including a quinacridone derivative represented by Chemical Formula 1:

[Chemical Formula 1]

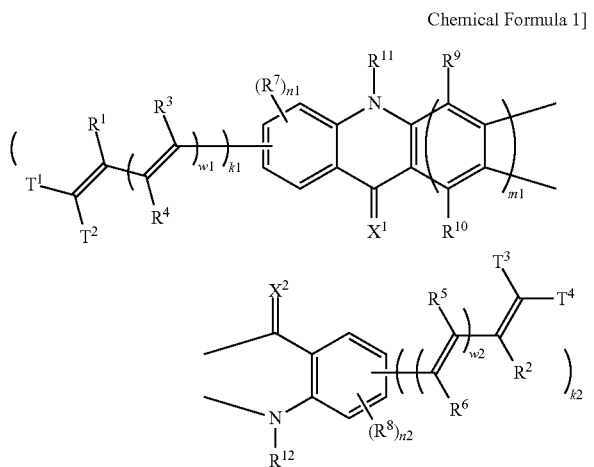

wherein, in Chemical Formula 1, $T^1$ to $T^4$ are one of same and different, and each of $T^1$ to $T^4$ are independently one of a cyano group (CN), a halogen, a substituted or unsubstituted $C_6$ to $C_{30}$ aryl group, and a substituted or unsubstituted $C_2$ to $C_{30}$ heteroaryl group, $X^1$ and $X^2$ are one of same and different, and each of $X^1$ and $X^2$ are independently one of oxygen (O), sulfur (S), and $C(CN)_2$, $R^1$ to $R^{10}$ are one of same and different, and each of $R^1$ to $R^{10}$ are independently one of hydrogen, a substituted or unsubstituted $C_1$ to $C_{30}$ alkyl group, a substituted or unsubstituted $C_3$ to $C_{30}$ cycloalkyl group, a cyano group (CN), a halogen, a substituted or unsubstituted $C_6$ to $C_{30}$ aryl group, and a substituted or unsubstituted $C_2$ to $C_{30}$ heteroaryl group, wherein at least one of $R^1$ and $R^2$ is not hydrogen, w1 and w2 are each independently an integer ranging from 0 to 5, k1 and k2 are each independently an integer ranging from 1 to 4, n1 and n2 are each independently an integer ranging from 0 to 3, m1 is an integer ranging from 1 to 5, and $R^{11}$ and $R^{12}$ are one of same and different, and each of $R^{11}$ and $R^{12}$ are independently one of hydrogen, a substituted or unsubstituted $C_1$ to $C_{30}$ alkyl group, and a substituted or unsubstituted $C_3$ to $C_{30}$ cycloalkyl group.

2. The photoelectric conversion device of claim 1, wherein the photoactive layer includes one selected from a p layer, an i layer, an n layer, and a combination thereof.

3. The photoelectric conversion device of claim 2, wherein the quinacridone derivative is a p-type material, and a material with a LUMO level lower than about −5.0 eV is an n-type material, and the quinacridone derivative is included in one selected from the p layer, the i layer, and a combination thereof, and the n-type material is included in one selected from the i layer, the n layer, and a combination thereof.

4. The photoelectric conversion device of claim 2, wherein the quinacridone derivative is an n-type material, and a material with a LUMO level higher than −2.0 eV is a p-type material, and the quinacridone derivative is included in one selected from the i layer, the n layer, and a combination thereof, and the p-type material is included in one selected from the p layer, the i layer, and a combination thereof.

5. The photoelectric conversion device of claim 1, wherein the photoelectric conversion device includes a photodiode, a solar cell, an image sensing device, a photodetector, a photosensor, or an organic light emitting diode (OLED).

6. The photoelectric conversion device of claim 1, wherein $T^1$ to $T^4$ are one of same and different, and each of $T^1$ to $T^4$ are independently one of a cyano group (CN) and a halogen, $X^1$ and $X^2$ are one of same and different, and each of $X^1$ and $X^2$ are independently one of oxygen (O) and sulfur (S), $R^1$ to $R^{10}$ are one of same and different, and each of $R^1$ to $R^{10}$ are independently one of hydrogen, a substituted or unsubstituted $C_1$ to $C_{10}$ alkyl group, a substituted or unsubstituted $C_3$ to $C_{10}$ cycloalkyl group, a cyano group (CN), and a halogen, wherein at least one of $R^1$ and $R^2$ is not hydrogen, w1 and w2 are each independently an integer of 0 or 1, k1 and k2 are each independently an integer of 1 or 2, n1 and n2 are each independently an integer ranging from 0 to 3, m1 is an integer ranging from 1 to 3, and $R^{11}$ and $R^{12}$ are one of same and different, and each of $R^{11}$ and $R^{12}$ are independently one of hydrogen, a substituted or unsubstituted $C_1$ to $C_{10}$ alkyl group, and a substituted or unsubstituted $C_3$ to $C_{10}$ cycloalkyl group.

7. The photoelectric conversion device of claim 1, wherein the quinacridone derivative includes one selected from compounds according to Chemical Formulas 2-7, 2-8 and a combination thereof:

[Chemical Formula 2-7]

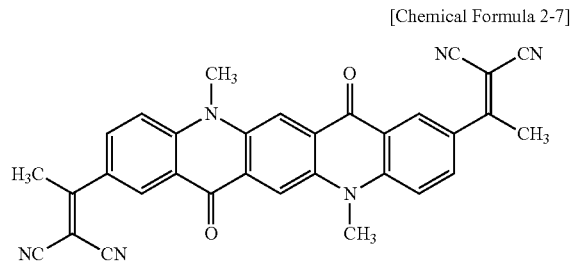

[Chemical Formula 2-8]

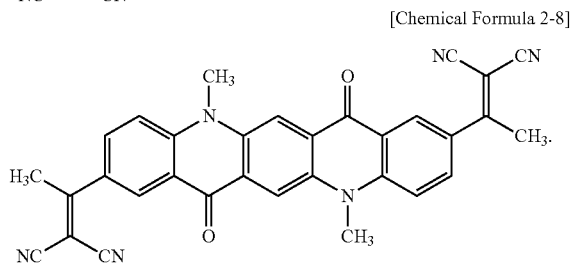

8. The photoelectric conversion device of claim 1, wherein the quinacridone derivative is represented by Chemical Formula 2-9:

[Chemical Formula 2-9]

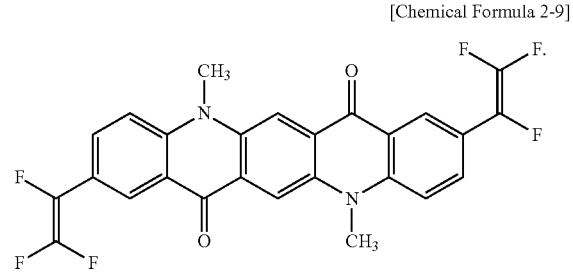 [SMILES: Cn1c2ccc(C(F)=C(F)F)cc2c(=O)c2cc3c(cc21)c(=O)c1cc(C(F)=C(F)F)ccc1n3C]

9. The photoelectric conversion device of claim 1, wherein the quinacridone derivative has a LUMO (lowest unoccupied molecular orbital) level ranging from about −2.0 eV to about −5.0 eV.

10. The photoelectric conversion device of claim 1, wherein the quinacridone derivative has a bandgap ranging from about 1.5 eV to about 3.5 eV.

11. The photoelectric conversion device of claim 1, wherein the quinacridone derivative has a maximum molar absorption coefficient of about $5.0 \times 10^2$ cm$^{-1}\cdot$M$^{-1}$ to about $1.0 \times 10^6$ cm$^{-1}\cdot$M$^{-1}$.

12. A photoelectric conversion device, comprising:
a first electrode;
a second electrode spaced apart from and configured to face the first electrode; and
a photoactive layer between the first electrode and the second electrode, the photoactive layer including a quinacridone derivative represented by Chemical Formula 1:

13. The photoelectric conversion device of claim 12, wherein $T^1$ to $T^4$ are one of same and different, and each of $T^1$ to $T^4$ are independently one of a cyano group (CN) and a halogen,
$X^1$ and $X^2$ are one of same and different, and each of $X^1$ and $X^2$ are independently one of oxygen (O) and sulfur (S),
$R^1$ to $R^{10}$ are one of same and different, and each of $R^1$ to $R^{10}$ are independently one of hydrogen, a substituted or unsubstituted $C_1$ to $C_{10}$ alkyl group, a substituted or unsubstituted $C_3$ to $C_{10}$ cycloalkyl group, a cyano group (CN), and a halogen, w1 and w2 are each independently an integer of 0 or 1,
k1 and k2 are each independently an integer of 1 or 2,
n1 and n2 are each independently an integer ranging from 0 to 3,
m1 is an integer ranging from 2 to 3, and
$R^{11}$ and $R^{12}$ are one of same and different, and each of $R^{11}$ and $R^{12}$ are independently one of hydrogen, a substi-

[Chemical Formula 1]

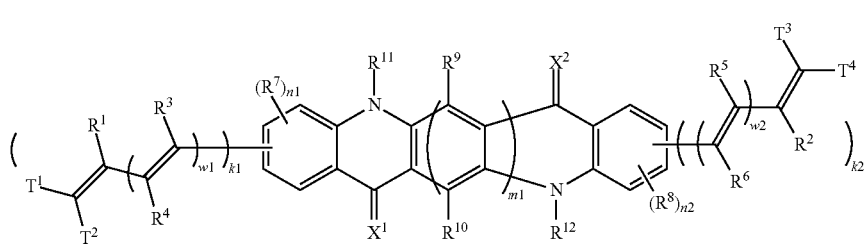

wherein, in Chemical Formula 1,
$T^1$ to $T^4$ are one of same and different, and each of $T^1$ to $T^4$ are independently one of a cyano group (CN), a halogen, a substituted or unsubstituted $C_6$ to $C_{30}$ aryl group, and a substituted or unsubstituted $C_2$ to $C_{30}$ heteroaryl group,
$X^1$ and $X^2$ are one of same and different, and each of $X^1$ and $X^2$ are independently one of oxygen (O), sulfur (S), and $C(CN)_2$,
$R^1$ to $R^{10}$ are one of same and different, and each of $R^1$ to $R^{10}$ are independently one of hydrogen, a substituted or unsubstituted $C_1$ to $C_{30}$ alkyl group, a substituted or unsubstituted $C_3$ to $C_{30}$ cycloalkyl group, a cyano group (CN), a halogen, a substituted or unsubstituted $C_6$ to $C_{30}$ aryl group, and a substituted or unsubstituted $C_2$ to $C_{30}$ heteroaryl group,
w1 and w2 are each independently an integer ranging from 0 to 5,
k1 and k2 are each independently an integer ranging from 1 to 4,
n1 and n2 are each independently an integer ranging from 0 to 3,
m1 is an integer ranging from 2 to 5, and
$R^{11}$ and $R^{12}$ are one of same and different, and each of $R^{11}$ and $R^{12}$ are independently one of hydrogen, a substituted or unsubstituted $C_1$ to $C_{30}$ alkyl group, and a substituted or unsubstituted $C_3$ to $C_{30}$ cycloalkyl group.

tuted or unsubstituted $C_1$ to $C_{10}$ alkyl group, and a substituted or unsubstituted $C_3$ to $C_{10}$ cycloalkyl group.

14. The photoelectric conversion device of claim 12, wherein the quinacridone derivative is represented by Chemical Formula 2-10:

[Chemical Formula 2-10]

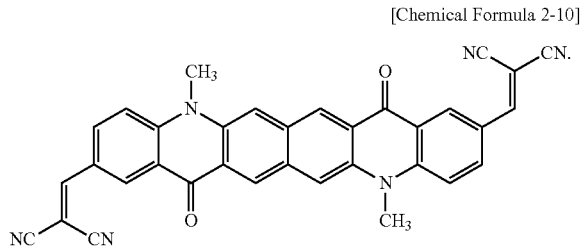 [SMILES: Cn1c2ccc(C=C(C#N)C#N)cc2c(=O)c2cc3cc4c(cc3cc21)c(=O)c1cc(C=C(C#N)C#N)ccc1n4C]

15. A photoelectric conversion device, comprising:
a first electrode;
a second electrode spaced apart from and configured to face the first electrode; and
a photoactive layer between the first electrode and the second electrode, the photoactive layer including a quinacridone derivative represented by Chemical Formula 1:

[Chemical Formula 1]

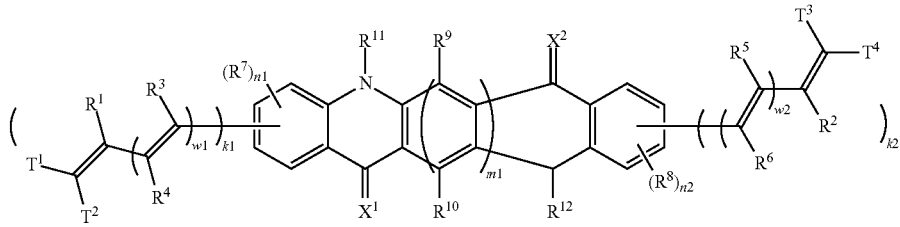

wherein, in Chemical Formula 1, $T^1$ to $T^4$ are one of same and different, and each of $T^1$ to $T^4$ are independently one of a cyano group (CN), a halogen, a substituted or unsubstituted $C_6$ to $C_{30}$ aryl group, and a substituted or unsubstituted $C_2$ to $C_{30}$ heteroaryl group, $X^1$ and $X^2$ are one of same and different, and each of $X^1$ and $X^2$ are independently one of sulfur (S) and $C(CN)_2$, $R^1$ to $R^{10}$ are one of same and different, and each of $R^1$ to $R^{10}$ are independently one of hydrogen, a substituted or unsubstituted $C_1$ to $C_{30}$ alkyl group, a substituted or unsubstituted $C_3$ to $C_{30}$ cycloalkyl group, a cyano group (CN), a halogen, a substituted or unsubstituted $C_6$ to $C_{30}$ aryl group, and a substituted or unsubstituted $C_2$ to $C_{30}$ heteroaryl group, w1 and w2 are each independently an integer ranging from 0 to 5, k1 and k2 are each independently an integer ranging from 1 to 4, n1 and n2 are each independently an integer ranging from 0 to 3, m1 is an integer ranging from 1 to 5, and $R^{11}$ and $R^{12}$ are one of same and different, and each of $R^{11}$ and $R^{12}$ are independently one of hydrogen, a substituted or unsubstituted $C_1$ to $C_{30}$ alkyl group, and a substituted or unsubstituted $C_3$ to $C_{30}$ cycloalkyl group.

16. The photoelectric conversion device of claim 15, wherein $T^1$ to $T^4$ are one of same and different, and each of $T^1$ to $T^4$ are independently one of a cyano group (CN) and a halogen, each of $X^1$ and $X^2$ are sulfur (S), $R^1$ to $R^{10}$ are one of same and different, and each of $R^1$ to $R^{10}$ are independently one of hydrogen, a substituted or unsubstituted $C_1$ to $C_{10}$ alkyl group, a substituted or unsubstituted $C_3$ to $C_{10}$ cycloalkyl group, a cyano group (CN), and a halogen, w1 and w2 are each independently an integer of 0 or 1, k1 and k2 are each independently an integer of 1 or 2, n1 and n2 are each independently an integer ranging from 0 to 3, m1 is an integer ranging from 1 to 3, and $R^{11}$ and $R^{12}$ are one of same and different, and each of $R^{11}$ and $R^{12}$ are independently one of hydrogen, a substituted or unsubstituted $C_1$ to $C_{10}$ alkyl group, and a substituted or unsubstituted $C_3$ to $C_{10}$ cycloalkyl group.

17. The photoelectric conversion device of claim 15, wherein the quinacridone derivative includes one selected from compounds according to Chemical Formulas 2-5, 2-6 and a combination thereof:

[Chemical Formula 2-5]

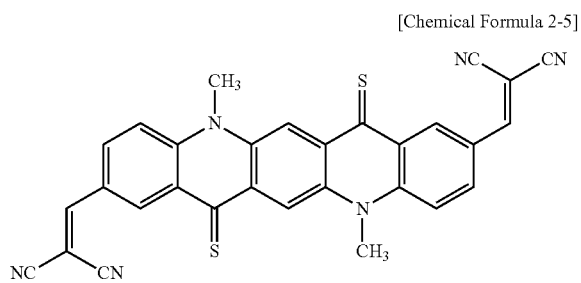

[Chemical Formula 2-6]

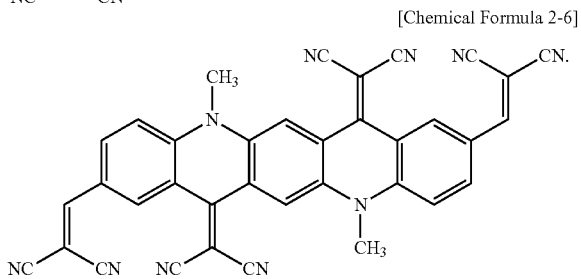

18. A photoelectric conversion device, comprising:
a first electrode;
a second electrode spaced apart from and configured to face the first electrode; and
a photoactive layer between the first electrode and the second electrode, the photoactive layer including a quinacridone derivative represented by Chemical Formula 1:

[Chemical Formula 1]

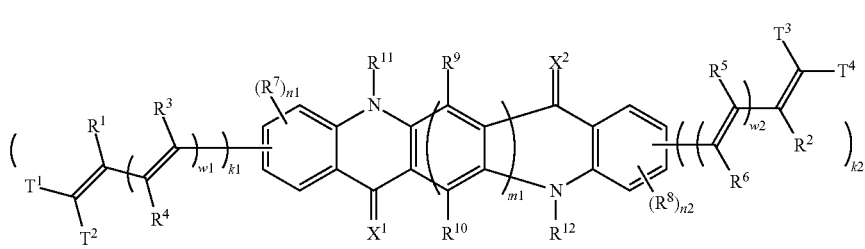

wherein, in Chemical Formula 1,

T$^1$ to T$^4$ are one of same and different, and each of T$^1$ to T$^4$ are independently one of a cyano group (CN), a halogen, a substituted or unsubstituted C$_6$ to C$_{30}$ aryl group, and a substituted or unsubstituted C$_2$ to C$_{30}$ heteroaryl group, X$^1$ and X$^2$ are one of same and different, and each of X$^1$ and X$^2$ are independently one of oxygen, sulfur (S) and C(CN)$_2$, R$^1$ to R$^{10}$ are one of same and different, and each of R$^1$ to R$^{10}$ are independently one of hydrogen, a substituted or unsubstituted C$_1$ to C$_{30}$ alkyl group, a substituted or unsubstituted C$_3$ to C$_{30}$ cycloalkyl group, a cyano group (CN), a halogen, a substituted or unsubstituted C$_6$ to C$_{30}$ aryl group, and a substituted or unsubstituted C$_2$ to C$_{30}$ heteroaryl group, w1 and w2 are each independently an integer ranging from 0 to 5, k1 and k2 are each independently an integer ranging from 1 to 4, n1 and n2 are each independently an integer ranging from 0 to 3, wherein at least one of n1 and n2 is an integer ranging from 2 to 3, m1 is an integer ranging from 1 to 5, and R$^{11}$ and R$^{12}$ are one of same and different, and each of R$^{11}$ and R$^{12}$ are independently one of hydrogen, a substituted or unsubstituted C$_1$ to C$_{30}$ alkyl group, and a substituted or unsubstituted C$_3$ to C$_{30}$ cycloalkyl group.

19. The photoelectric conversion device of claim 18, wherein T$^1$ to T$^4$ are one of same and different, and each of T$^1$ to T$^4$ are independently one of a cyano group (CN) and a halogen, X$^1$ and X$^2$ are one of same and different, and each of X$^1$ and X$^2$ are independently one of oxygen (O) and sulfur (S), R$^1$ to R$^{10}$ are one of same and different, and each of R$^1$ to R$^{10}$ are independently one of hydrogen, a substituted or unsubstituted C$_1$ to C$_{10}$ alkyl group, a substituted or unsubstituted C$_3$ to C$_{10}$ cycloalkyl group, a cyano group (CN), and a halogen, w1 and w2 are each independently an integer of 0 or 1, k1 and k2 are each independently an integer of 1 or 2, m1 is an integer ranging from 1 to 3, and R$^{11}$ and R$^{12}$ are one of same and different, and each of R$^{11}$ and R$^{12}$ are independently one of hydrogen, a substituted or unsubstituted C$_1$ to C$_{10}$ alkyl group, and a substituted or unsubstituted C$_3$ to C$_{10}$ cycloalkyl group.

20. The photoelectric conversion device of claim 18, wherein the quinacridone derivative is represented by Chemical Formula 2-4:

[Chemical Formula 2-4]

21. A photoelectric conversion device, comprising:
a first electrode;
a second electrode spaced apart from and configured to face the first electrode; and
a photoactive layer between the first electrode and the second electrode, the photoactive layer including a quinacridone derivative represented by Chemical Formula 1:

[Chemical Formula 1]

wherein, in Chemical Formula 1,

T$^1$ to T$^4$ are one of same and different, and each of T$^1$ to T$^4$ are independently one of a halogen, a substituted or unsubstituted C$_6$ to C$_{30}$ aryl group, and a substituted or unsubstituted C$_2$ to C$_{30}$ heteroaryl group, X$^1$ and X$^2$ are one of same and different, and each of X$^1$ and X$^2$ are independently one of oxygen, sulfur (S) and C(CN)$_2$, R$^1$ to R$^{10}$ are one of same and different, and each of R$^1$ to R$^{10}$ are independently one of hydrogen, a substituted or unsubstituted C$_1$ to C$_{30}$ alkyl group, a substituted or unsubstituted C$_3$ to C$_{30}$ cycloalkyl group, a cyano group (CN), a halogen, a substituted or unsubstituted C$_6$ to C$_{30}$ aryl group, and a substituted or unsubstituted C$_2$ to C$_{30}$ heteroaryl group, w1 and w2 are each independently an integer ranging from 0 to 5, k1 and k2 are each independently an integer ranging from 1 to 4, n1 and n2 are each independently an integer ranging from 0 to 3, m1 is an integer ranging from 1 to 5, and R$^{11}$ and R$^{12}$ are one of same and different, and each of R$^{11}$ and R$^{12}$ are independently one of hydrogen, a substituted or unsubstituted C$_1$ to C$_{30}$ alkyl group, and a substituted or unsubstituted C$_3$ to C$_{30}$ cycloalkyl group.

22. The photoelectric conversion device of claim 21, wherein each of T$^1$ to T$^4$ are a halogen, X$^1$ and X$^2$ are one of same and different, and each of X$^1$ and X$^2$ are independently one of oxygen (O) and sulfur (S), $R^1$ to $R^{10}$ are one of same and different, and each of $R^1$ to $R^{10}$ are independently one of hydrogen, a substituted or unsubstituted $C_1$ to $C_{10}$ alkyl group, a substituted or unsubstituted $C_3$ to $C_{10}$ cycloalkyl group, a cyano group (CN), and a halogen, w1 and w2 are each independently an integer of 0 or 1, k1 and k2 are each independently an integer of 1 or 2, n1 and n2 are each independently an integer ranging from 0 to 3, wherein at least one of n1 and n2 is an integer ranging from 2 to 3, m1 is an integer ranging from 1 to 3, and $R^{11}$ and $R^{12}$ are one of same and different, and each of $R^{11}$ and $R^{12}$ are independently one of hydrogen, a substituted or unsubstituted $C_1$ to $C_{10}$ alkyl group, and a substituted or unsubstituted $C_3$ to $C_{10}$ cycloalkyl group.

23. The photoelectric conversion device of claim 21, wherein the quinacridone derivative is represented by Chemical Formula 2-9:

[Chemical Formula 2-9]

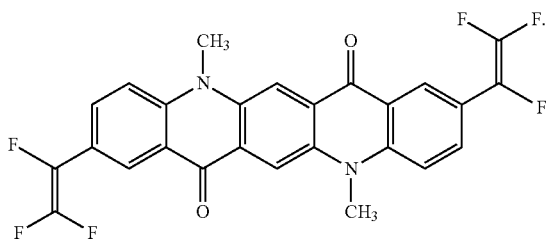

24. A photoelectric conversion device, comprising:
a first electrode;
a second electrode spaced apart from and configured to face the first electrode; and
a photoactive layer between the first electrode and the second electrode, the photoactive layer including a quinacridone derivative represented by Chemical Formula 1:

wherein, in Chemical Formula 1, $T^1$ to $T^4$ are one of same and different, and each of $T^1$ to $T^4$ are independently one of a cyano group (CN), a halogen, a substituted or unsubstituted $C_6$ to $C_{30}$ aryl group, and a substituted or unsubstituted $C_2$ to $C_{30}$ heteroaryl group, $X^1$ and $X^2$ are one of same and different, and each of $X^1$ and $X^2$ are independently one of oxygen, sulfur (S) and $C(CN)_2$, $R^1$ to $R^{10}$ are one of same and different, and each of $R^1$ to $R^{10}$ are independently one of hydrogen, a substituted or unsubstituted $C_1$ to $C_{30}$ alkyl group, a substituted or unsubstituted $C_3$ to $C_{30}$ cycloalkyl group, a cyano group (CN), a halogen, a substituted or unsubstituted $C_6$ to $C_{30}$ aryl group, and a substituted or unsubstituted $C_2$ to $C_{30}$ heteroaryl group, w1 and w2 are each independently an integer ranging from 0 to 5, k1 and k2 are each independently an integer ranging from 1 to 4, n1 and n2 are each independently an integer ranging from 0 to 3, m1 is an integer ranging from 1 to 5, and $R^{11}$ and $R^{12}$ are one of same and different, and each of $R^{11}$ and $R^{12}$ are independently one of a substituted or unsubstituted $C_2$ to $C_{30}$ alkyl group, and a substituted or unsubstituted $C_3$ to $C_{30}$ cycloalkyl group.

25. The photoelectric conversion device of claim 24, wherein $T^1$ to $T^4$ are one of same and different, and each of $T^1$ to $T^4$ are independently one of a cyano group (CN) and a halogen, $X^1$ and $X^2$ are one of same and different, and each of $X^1$ and $X^2$ are independently one of oxygen (O) and sulfur (S), $R^1$ to $R^{10}$ are one of same and different, and each of $R^1$ to $R^{10}$ are independently one of hydrogen, a substituted or unsubstituted $C_1$ to $C_{10}$ alkyl group, a substituted or unsubstituted $C_3$ to $C_{10}$ cycloalkyl group, a cyano group (CN), and a halogen, wherein at least one of $R^1$ and $R^2$ is not a cyano group (CN), w1 and w2 are each independently an integer of 0 or 1, k1 and k2 are each independently an integer of 1 or 2, n1 and n2 are each independently an integer ranging from 0 to 3, wherein at least one of n1 and n2 is an integer ranging from 2 to 3,

[Chemical Formula 1]

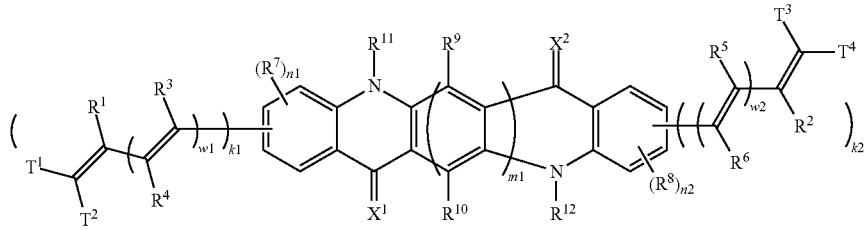

m1 is an integer ranging from 1 to 3, and $R^{11}$ and $R^{12}$ are one of same and different, and each of $R^{11}$ and $R^{12}$ are independently one of a substituted or unsubstituted $C_2$ to $C_{10}$ alkyl group, and a substituted or unsubstituted $C_3$ to $C_{10}$ cycloalkyl group.

26. The photoelectric conversion device of claim 24, wherein the quinacridone derivative is represented by Chemical Formula 2-3:

[Chemical Formula 2-3]
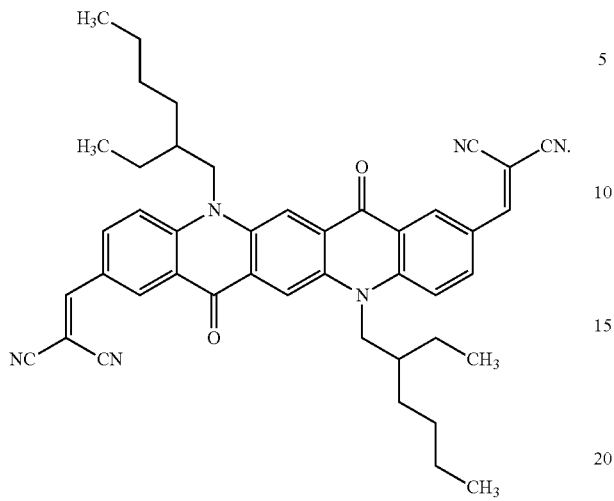
* * * * *